United States Patent
Yamato et al.

(10) Patent No.: US 7,244,419 B2
(45) Date of Patent: Jul. 17, 2007

(54) GELLING AGENT FOR OIL

(75) Inventors: Naoya Yamato, Kawasaki (JP); Hideki Yoshihara, Yokkaichi (JP)

(73) Assignee: Ajinomoto Co., Inc., Tokyo (JP)

( * ) Notice: Subject to any disclaimer, the term of this patent is extended or adjusted under 35 U.S.C. 154(b) by 170 days.

(21) Appl. No.: 10/871,024

(22) Filed: Jun. 21, 2004

(65) Prior Publication Data
US 2004/0229984 A1 Nov. 18, 2004

Related U.S. Application Data

(62) Division of application No. 10/073,226, filed on Feb. 13, 2002, now abandoned.

(30) Foreign Application Priority Data
Feb. 13, 2001 (JP) ............................. 2001-035011

(51) Int. Cl.
*A61K 7/32* (2006.01)
*A61K 7/38* (2006.01)
(52) U.S. Cl. ........................... 424/67; 424/66; 554/35; 554/57
(58) Field of Classification Search ................ 554/57, 554/35; 424/66, 67
See application file for complete search history.

(56) References Cited

U.S. PATENT DOCUMENTS

| 3,969,087 A | 7/1976 | Saito et al. |
| 5,591,424 A | 1/1997 | Hofrichter et al. |
| 2002/0159961 A1 | 10/2002 | Yamato et al. |
| 2004/0229984 A1 | 11/2004 | Yamato et al. |
| 2005/0100572 A1 | 5/2005 | Hatajima et al. |

FOREIGN PATENT DOCUMENTS

| EP | 0 665 250 A1 | 8/1995 |
| EP | 0 896 048 A1 | 2/1999 |
| JP | 51-19139 | 2/1976 |
| JP | 7-506833 | 7/1995 |
| WO | WO 03/023008 | 11/1993 |

OTHER PUBLICATIONS

Decanoic acid, 1-carboxyethyl ester, Database: Registry, RN:5119-25-6.*
Decanoic acid, Database:Registry, RN:334-48-5.*
L-Glutamic acid, N-(1-oxodecyl)-, Database:Registy, RN:111276-71-2.*
Sakura color products corp., Water-in-oil emulsion inks, Patent Abstract, JP 57202360 (Japan), 1982.
Higeta et al, Glutamic acid diamide . . . , Patent Abstract, JP04372671 (Japan), 1992.
U.S. Appl. No. 11/281,601, filed Nov. 18, 2005, Yamato.
U.S. Appl. No. 11/002,117, filed Dec. 3, 2004, Yamato et al.

* cited by examiner

*Primary Examiner*—Vickie Kim
(74) *Attorney, Agent, or Firm*—Oblon, Spivak, McClelland, Maier & Neustadt, P.C.

(57) ABSTRACT

A compound represented by the following general formula (I), wherein $R^1$ and $R^2$ represent a hydrocarbon group having 1 to 26 carbon atoms, preferably a linear or branched alkyl group, $R^3$ represents a hydrocarbon group having 7 to 10 carbon atoms, preferably a linear or branched alkyl group, n represents 1 or 2 provided that the acidic amino acid residue in the molecule is L-aspartic acid residue when n is 1 and said acidic amino acid residue is L-glutamic acid residue when n is 2, and a gelling agent for an oil comprising said compound (I)

$$R^3-\underset{\underset{H}{|}}{C(=O)}-N-CH(CONHR^2)-(CH_2)_n-CONHR^1$$

14 Claims, No Drawings

GELLING AGENT FOR OIL

This application is a divisional of U.S. Ser. No. 10/073,226, which was filed on Feb. 13, 2002, now abandoned which claims priority to JP 2001-035011, filed on Feb. 13, 2001.

BACKGROUND OF THE INVENTION

1. Field of the Invention

The present invention relates to a gelling agent for an oil. More specifically, the present invention relates to a gelling agent for an oil which contains a particular class of an amino acid derivative. The gelling agent of the present invention is useful for gelling an oil in a state of a liquid at an ordinary temperature to obtain variety forms of the oil.

2. Related Art

As gelling agents for an oil that is insoluble in water, for example, polyamide resins, 12-hydroxystearic acid, condensates of an aromatic aldehyde and a polyhydric alcohol whose typical example includes dibenzylidene-D-sorbitol and the like have been known so far. However, these gelling agents have a problem of low solubility in oils. For example, gel compositions prepared by using these gelling agents have a problem of poor stability in a dissolved state, which results in formation of heterogeneous gel compositions or so-called "sweating phenomenon" as exudation of the gelled oils form the surfaces of the gels due to degradation with time.

As another gelling agent for an oil, N-lauroyl-L-glutamic acid dibutylamide disclosed in Japanese Patent Unexamined Publication (Kokai) No. 51-19139/1976 is known, and cosmetics containing said substance as a gelling agent have been reported. The aforementioned gelling agent can form gels from variety of types of oils. However, gel compositions obtained sometimes fail to have sufficient gel strength. As a result, when gel compositions are prepared as cosmetics for dermal application, the compositions may sometimes become tender and have a problem from a viewpoint of strength.

Furthermore, U.S. Pat. No. 5,591,424 and International Patent Publication in Japanese (Kohyo) No. 7-506833 disclose antiperspirant gel sticks containing 12-hydroxystearic acid and N-lauroylglutamic acid dibutylamide. However, the aforementioned gel sticks are also insufficient in strength, and the sticks may sometimes have difficulty in application to the skin. Moreover, appearance of each gel composition obtained by using the gelling agent and an oil is white and lacks transparency, which is not desired from an esthetic viewpoint.

SUMMARY OF THE INVENTION

An object of the present invention is to provide a gelling agent for an oil. More specifically, the object of the present invention is to provide a gelling agent that has superior gel forming ability for an oil. Another object of the present invention is to provide a gelling agent that enables production of a gel composition having superior gel strength and transparency. A still further object of the present invention is to provide a gel composition which comprises a gelling agent having the aforementioned characteristics and an oil and has superior gel strength and transparency.

The inventors of the present invention conducted various studies to achieve the aforementioned objects. As a result, they found that a particular class of acidic amino acid derivatives had unexpectedly excellent properties as a gelling agent for an oil, and gel compositions prepared from these acidic amino acid derivatives and an oil had superior gel strength and high transparency. They also found that the resulting gel compositions had satisfactory strength for applications as cosmetics, and that the compositions were easily applicable to the skin when they are made into a stick form or the like. The present invention was achieved on the basis of the aforementioned findings.

The present invention thus provides a compound represented by the following general formula (I):

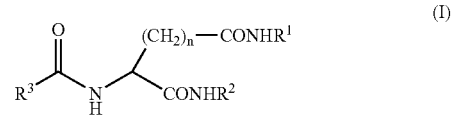

wherein $R^1$ and $R^2$ independently represent a hydrocarbon group having 1 to 26 carbon atoms; $R^3$ represents a hydrocarbon group having 7 to 10 carbon atoms; n represents 1 or 2 provided that the acidic amino acid residue in the molecule is L-aspartic acid residue when n is 1 and said amino acid residue is L-glutamic acid residue when n is 2.

According to a preferred embodiment of the present invention, provided is the aforementioned compound wherein $R^1$ and $R^2$ independently represents a linear or branched alkyl group having 1 to 26 carbon atoms; $R^3$ represents a linear or branched alkyl group having 7 to 10 carbon atoms; and n represents 2. According to a more preferred embodiment of the present invention, provided is the aforementioned compound wherein $R^1$ and $R^2$ independently represents a linear or branched alkyl group having 3 to 5 carbon atoms, $R^3$ represents a linear or branched alkyl group having 7 to 9 carbon atoms, and n represents 2. As a particularly preferred embodiment of the present invention, provided are N-2-ethylhexanoyl-L-glutamic acid dibutylamide, N-octanoyl-L-glutamic acid dibutylamide, and N-decanoyl-L-glutamic acid dibutylamide which are compounds falling within the scope of the aforementioned general formula (I).

From further aspects of the present invention, provided are a gelling agent for an oil which comprises at least one kind of a compound represented by the aforementioned general formula (I); and a gelling agent for an oil which comprises at least one kind of a compound represented by the aforementioned general formula (I) together with N-lauroyl-L-glutamic acid dibutylamide. As preferred examples of the latter invention, provided is the aforementioned gelling agent wherein a ratio of total weight of the compound represented by the aforementioned general formula (I) and weight of N-lauroyl-L-glutamic acid dibutylamide is 35:5 to 5:35.

From still further aspect of the present invention, provided is a gel composition which comprises (a) the aforementioned gelling agent, and (b) at least one oil. According to preferred embodiments of the aforementioned gel composition, provided are the gel composition as a translucent composition, and the gel composition which further comprises (c) at least one active ingredient as an antiperspirant. Further, the present invention also provides a cosmetic comprising the aforementioned gel composition. Preferably, the cosmetic may be cast in a form of a stick.

The present invention further provides a method for gel formation from an oil, which comprises the step of mixing at least one compound represented by the aforementioned general formula (I) with an oil optionally together with N-lauroyl-L-glutamic acid dibutylamide; a method for preparing a gel composition comprising an oil which comprise the step of mixing at least one compound represented by the aforementioned general formula (I) with an oil optionally together with N-lauroyl-L-glutamic acid dibutylamide; and use of the compound represented by the aforementioned general formula (I) for preparation of a gel composition comprising an oil.

By using the gelling agent of the present invention for an oil, a gel composition having high gel strength and superior transparency can be produced.

PREFERRED EMBODIMENTS OF THE INVENTION

In the general formula (I), $R^1$ and $R^2$ independently represent a hydrocarbon group having 1 to 26 carbon atoms. The hydrocarbon group represented by $R^1$ or $R^2$ may be linear, branched, cyclic, or a combination thereof. As the hydrocarbon group, a hydrocarbon group containing an unsaturated bond may be used; however, an alkyl group may preferably be used as the hydrocarbon group. A linear or branched alkyl group having preferably 1 to 10 carbon atoms, more preferably 2 to 6 carbon atoms, may be used, and a linear or branched alkyl group having 3 to 5 carbon atoms is more preferred. n-Butyl group may most preferably be used.

$R^3$ represents a hydrocarbon group having 7 to 10 carbon atoms. The hydrocarbon group represented by $R^3$ may be linear, branched, cyclic, or a combination thereof. As the hydrocarbon group, a hydrocarbon group containing an unsaturated bond may be used; however, an alkyl group may preferably be used as the hydrocarbon group. As the alkyl group, a linear or branched alkyl group is preferred. More preferably, $R^3$ represents a linear or branched alkyl group having 7 to 9 carbon atoms. Examples of the group represented by $R^3$—CO— include, for example, n-octanoyl group, n-nonanoyl group, n-decanoyl group, n-undecanoyl group, 2-ethylhexanoyl group and the like. Among them, octanoyl group, decanoyl group, and 2-ethylhexanoyl group are preferred, and 2-ethylhexanoyl group is more preferred from a viewpoint of high gel forming ability for variety of oils. When the group represented by $R^3$—CO— is 2-ethylhexanoyl group, 2-(R,S)-ethylhexanoyl group is preferably used from a viewpoint of availability of 2-ethylhexanoyl chloride as a starting material. In the general formula (I), n is preferably 2.

In the compound represented by the general formula (I), the acidic amino acid residue in the molecule is L-aspartic acid residue when n is 1, or acidic amino acid residue is L-glutamic acid residue when n is 2. The compound represented by the general formula (I) may have one or more asymmetric carbons depending on types of $R^1$, $R^2$ and/or $R^3$. Any of stereoisomers such as optical isomers and diastereomers based on such asymmetric carbons, any mixtures of the stereoisomers, and racemates fall within the scope of the present invention. Further, when $R^1$, $R^2$ and/or $R^3$ have an olefinic double bond, its configuration may be in either Z- or E-configuration, and geometrical isomers and any mixtures of the geometrical isomers also fall within the scope of the present invention. In addition, any hydrates and any forms of crystals of the compound represented by the aforementioned general formula (I) also fall within the scope of the present invention. As the gelling agent of the present invention, any substance such as the aforementioned isomers, mixtures thereof, hydrates thereof and the like can be used.

The compound represented by the general formula (I) can be produced by, for example, reacting a long chain fatty acid halide with L-glutamic acid or L-aspartic acid in the presence of a basic catalyst according to the Schotten Baumann's reaction to prepare an N-acylated glutamic acid or N-acylated aspartic acid, and then reacting the resulting product with an amine derivative such as alkylamines in the presence of an acid catalyst or in the absence of a catalyst with heating. Alternatively, the target compound can be produced by reacting glutamic acid or an aspartic acid with an amine derivative such as alkylamines in the presence of an acid catalyst or in the absence of a catalyst, and then subjecting the resulting glutamic acid amide or aspartic acid amide to N-acylation by using an acylating agent such as aliphatic acid halides.

Preparations of the compounds represented by the general formula (I) are explained specifically and in detail in the examples of the specification. Therefore, those skilled in the art can produce any of the compounds represented by the general formula (I) by referring to the preparation examples and appropriately choosing starting materials, regents, reaction conditions and the like, and applying appropriate modifications and alterations to the methods, as required.

As the gelling agent of the present invention, one kind of a compound selected from the compounds represented by the general formula (I) may be used. Two or more kinds of compounds selected from the compounds represented by the general formula (I) may also be used in combination. An amount of the gelling agent of the present invention is not particularly limited so long as the amount is sufficient for gel formation of an oil. Generally, the amount is about 0.1 to 15 parts by weight, preferably 1 to 10 parts by weight based on 100 parts by weight of an oil to be gelled. Where the amount is less than 0.1 part by weight, satisfactory gel strength may sometimes not be obtained. Where the amount is more than 15 parts by weight, the agent may not be dissolved in an oil, and appearance of a resulting gelled oil may sometimes be degraded.

The gelling agent of the present invention may contain N-lauroyl-L-glutamic acid dibutylamide in addition to one or more compounds selected from the compounds represented by the general formula (I). Where the aforementioned gelling agent is used, a gel composition having high gel strength and relatively high transparency (translucent) can be obtained. In the aforementioned embodiment, a mixing ratio of the total weight of the compound represented by the general formula (I) (as to the term "total weight" used in the specification, when one single compound is used, the term means the weight of the compound, or when two or more compounds are used, the term means the total sum of the weights of the compounds) and N-lauroyl-L-glutamic acid dibutylamide can be suitably selected depending on desired performances. Generally, the ratio may preferably be 35:5 to 5:35. An amount of the gelling agent containing N-lauroyl-L-glutamic acid dibutylamide is similar to that of the aforementioned gelling agent, and the amount may be 0.1 to 15 parts by weight, preferably 1 to 10 parts by weight based on 100 parts by weight of an oil to be gelled. N-Lauroyl-L-glutamic acid dibutylamide used for the present invention can be produced by the same method as the compounds represented by the aforementioned general formula (I), or said compound can also be obtained as a commercial product from Ajinomoto Co., Ltd (trade name: GP-1).

The oil used for the gel composition of the present invention is not particularly limited so long as the oil sufficiently dissolves the aforementioned gelling agent by heating and forms a gel when cooled to room temperature.

Specific examples thereof include silicone oils; higher alcohols such as cetyl alcohol, isostearyl alcohol, lauryl alcohol, hexadecyl alcohol and octyldodecanol; aliphatic acids such as isostearic acid, undecylenic acid and oleic acid; polyhydric alcohols such as glycerol, sorbitol, ethylene glycol, propylene glycol and polyethylene glycol; esters such as myristyl myristate, hexyl laurate, decyl oleate, isopropyl myristate, hexyldecyl dimethyloctanoate, glyceryl monostearate, diethyl phthalate, ethylene glycol monostearate and octyl oxystearate; hydrocarbons such as liquid paraffin, vaseline and squalane; waxes such as lanolin, reduced lanolin and carnauba wax; fats and oils such as mink oil, cacao oil, coconut oil, palm seed oil, camellia oil, sesame oil, castor oil and olive oil; ethylene/α-olefin co-oligomers and the like.

Examples of the silicone oils include silicone oils selected from the group consisting of methylpolysiloxane, highly polymerized methylpolysiloxane, ether-modified silicones such as polyoxyethylene/methylpolysiloxane copolymer, polyoxypropylene/methylpolysiloxane copolymer and poly(oxyethylene or oxypropylene)/methylpolysiloxane copolymer, stearoxymethylpolysiloxane, stearoxytrimethylsilane, methyl hydrogen polysiloxane, octamethylpolysiloxane, decamethylpolysiloxane, cyclic silicones such as decamethylcyclopentasiloxane, octamethylcyclotetrasiloxane, tetrahydrotetramethylcyclotetrasiloxane, methylcyclopolysiloxane, cyclopentasiloxane and dodecamethylcyclohexasiloxane; methylphenylpolysiloxane, trimethylsiloxy silicate, amino-modified silicones such as aminoethylaminopropylsiloxane/dimethylsiloxane copolymer, silanol-modified polysiloxanes, alkoxy-modified polysiloxanes, aliphatic acid-modified polysiloxanes, fluorine-modified polysiloxanes, epoxy-modified polysiloxanes, alkoxy-modified polysiloxane perfluoropolyethers, polyvinyl acetate dimethyl polysiloxane and mixtures thereof.

The oil is preferably used in a ratio of about 10 to 99.9% by weight based on the total weight of the gel composition. Where the amount of the oil is less than 10% by weight or more than 99.9% by weight, satisfactory gel strength may sometimes not be obtained.

The gel composition of the present invention may further contain an active ingredient as an antiperspirant (hereinafter referred to as "antiperspirant active ingredient"). In the specification, the "an antiperspirant active ingredient" means an ingredient that suppresses sweating by astringing the skin. However, the term should be construed in its widest sense, and the term must not be interpreted in any limitative way. Type of the antiperspirant active ingredient is not particularly limited, and two or more antiperspirant active ingredients may be used in combination. Examples of the antiperspirant active ingredient include chlorohydroxy aluminum, aluminum chloride, allantoin chlorohydroxy aluminum, aluminum sulfate, zinc oxide, zinc paraphenolsulfonate, zirconium aluminum complex produced by reacting zirconyl chloride with aluminum hydroxide and aluminum chlorohydroxide and the like. The antiperspirant active ingredient can be formulated in an amount of 1 to 60% by weight, preferably 5 to 35% by weight, based on the total weight of the gel composition. The antiperspirant active ingredient may be formulated in a form of either a solution or fine particles. When the antiperspirant active ingredient is used in the form of fine particles, particle size of a substance as the antiperspirant active ingredient may generally be about 1 to 100 microns, preferably about 1 to 50 microns, and said ingredient may preferably have a high bulk density.

Methods for producing the gel composition of the present invention are not particularly limit. For example, a desired gel composition can be obtained by heating the aforementioned gelling agent and an oil to a temperature of about 50 to 180° C. with stirring until the mixture became a uniform solution, and then cooling the resulting solution.

The gel composition of the present invention can be used as a cosmetic. When the gel composition of the present invention is used as a cosmetic, the aforementioned gel composition per se may be used. Generally, it is preferable to use the gel composition which is mixed with one or more types of ingredients ordinarily used for the manufacture of cosmetics.

Examples of ingredients to be formulated in cosmetics include, for example, various chelating agents for maintaining the effect of the aforementioned antiperspirant active ingredient and suppressing discoloration or generation of odor and the like. Types of the chelating agent are not particularly limited, and preferred examples thereof include chelating agents selected from the group consisting of triethylenetetramine, 1,1,1-trifluoro-3,2'-thenoylacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, Xylenol Orange, 5-sulfosalicylic acid, salicylic acid, pyrocatechol-3,5-disulfonate, 4,5-dihydroxybenzene-1,3-disulfonic acid, 1,2-diaminocyelohexane-N,N,N',N'-tetraacetic acid, citric acid, oxalate, nitrilotriacetic acid, ethylenediamine-N,N,N',N'-tetraacetic acid, acetylacetone and salts thereof, mixtures thereof and the like.

As other ingredients that can be formulated in cosmetics, one or more kinds of gelling agents other than the gelling agent of the present invention may be used in combination. Examples of such gelling agents include polyamide resins, 12-hydroxystearic acid, sodium stearate, dibenzylidene-D-sorbitol, N-lauroyl-L-glutamic acid dibutylamide and the like.

The cosmetic of the present invention may contain surfactants, various additives or various fine particles as other ingredients so far that the ingredients do not affect the advantageous effects of the present invention. As the surfactants, any of anionic surfactants, nonionic surfactants, cationic surfactants and ampholytic surfactants may be used. Examples of the anionic surfactants include, for example, N-long chain acyl amino acid salts such as N-long chain acyl acidic amino acid salts and N-long chain acyl neutral amino acid salts, N-long chain aliphatic acid acyl-N-methyltaurine acid salts, alkyl sulfates and alkylene oxide adducts thereof, aliphatic acid amide ether sulfates, metal salts and weak base salts of aliphatic acids, sulfosuccinic acid type surfactants, alkylphosphates and alkylene oxide adducts thereof, alkyl ether carboxylic acids and the like. Examples of the nonionic surfactants include, for example, ether type surfactants such as glycerol ethers and alkylene oxide adducts thereof, ester type surfactants such as glycerol esters and alkylene oxide adducts thereof, ether ester type surfactants such as sorbitan esters and alkylene oxide adducts thereof, ester type surfactants such as polyoxyalkylene aliphatic acid esters, glycerol esters, aliphatic acid polyglycerol esters, sorbitan esters and saccharose aliphatic acid esters, nitrogen-containing nonionic surfactants such as alkyl glucosides, hydrogenated castor oil pyroglutamic acid diesters and ethylene oxide adducts thereof, and aliphatic acid alkanolamides and the like. Examples of the cationic surfactants include, for example, aliphatic amine salts such as alkylammonium chlorides and dialkylammonium chlorides, quaternary ammonium salts thereof, aromatic quaternary ammonium salts such as benzalkonium salts, aliphatic acid acyl arginine esters and the like. Examples of the ampholytic surfactants include, for example, betaine type surfactants such as carboxybetaine, aminocarboxylic acid type surfactants, imidazoline type surfactants and the like.

Examples of various additives include, for example, amino acids such as glycine, alanine, serine, threonine, arginine, glutamic acid, aspartic acid, leucine and valine; polyhydric alcohols such as glycerol, ethylene glycol, 1,3-butylene glycol, propylene glycol and isoprene glycol; polyamino acids including polyglutamic acid and polyaspartic acid and salts thereof, water-soluble polymers such as polyethylene glycol, gum arabic, alginic acid salts, xanthane gum, hyaluronic acid, hyaluronic acid salts, chitin, chitosan, water-soluble chitin, carboxyvinyl polymers, carboxymethyl cellulose, hydroxyethyl cellulose, hydroxypropyltrimethyl ammonium chloride, poly(dimethylmethylene piperidium chloride), quaternary ammoniums of polyvinylpyrrolidone derivatives, cationized proteins, collagen decomposition products and derivatives thereof, acylated proteins and polyglycerol; sugar alcohols such as mannitol and alkylene oxide adducts thereof; lower alcohols such as ethanol and propanol as well as animal and plant extracts, nucleic acids, vitamins, enzymes, anti-inflammatory agents, antibacterial agents, preservatives, antioxidants, ultraviolet absorbers, chelating agents, antiperspirants, pigments, dyes, oxidation dyes, organic and inorganic fine particles, pH adjusting agents, pearling agents, wetting agents and the like.

Examples of various fine particles include, for example, resin fine particles such as nylon beads and silicone beads, nylon powder, aliphatic acid metal salt soap, yellow iron oxide, red iron oxide, black iron oxide, chrome oxide, cobalt oxide, carbon black, ultramarine blue, Berlin blue, zinc oxide, titanium oxide, zirconium oxide, silicon oxide, aluminum oxide, cerium oxide, mica-titanium, boron nitride, barium sulfate, calcium carbonate, magnesium carbonate, aluminum silicate, magnesium silicate, silicon carbide, dyes, lakes, sericite, mica, talc, kaolin, tabular barium sulfate, butterfly-shaped barium sulfate, microparticle titanium oxide, microparticle zinc oxide, microparticle iron oxide, acylamino acids such as acyllysine, acylglutamic acid, acylarginine and acylglycine and the like. Examples of usable fine particles also include the aforementioned fine particles which are subjected to a surface treatment such as silicone treatment, fluoro-compound treatment, silane coupling agent treatment, silanized organic titanate treatment, acylated lysine treatment, aliphatic acid treatment, metallic soap treatment, oil treatment, amino acid treatment and the like.

Purposes of use of the cosmetic of the present invention are not particularly limited. For example, the cosmetic can be used as a cosmetic in a form of, for example, a gel, a pack, a granule and the like. The cosmetic of the present invention can be manufactured by preparing the aforementioned gel composition, then adding and mixing one or more kinds of the additives explained above as required to form a uniform composition. Processes for the manufacture are not particularly limited, and any means available to those skilled in the art such as commonly and widely used means including mixing, stirring and kneading can be appropriately used.

EXAMPLES

The present invention will be explained more specifically with reference to the following examples. However, the present invention is not limited to the following examples.

Example 1

Preparation of N-2-(R,S)-ethylhexanoyl-L-glutamic acid dibutylamide 110 g of sodium glutamate monohydrate was dissolved in 140 g of water and 78 g of 27% aqueous sodium hydroxide and the solution was cooled to 10° C. The solution was added with 110 g of acetone and added dropwise with 87 g of 2-ethylhexanoyl chloride and 78 g of 27% aqueous sodium hydroxide. The reaction mixture for the acylation was diluted with 100 g of water and neutralized with 63 g of 95% sulfuric acid to separate an oil. The aqueous layer was removed, and the oil layer was concentrated under reduced pressure to obtain an oily substance. The resulting oily substance was dissolved in 742 g of methanol, and the solution was added with 6.2 g of 95% sulfuric acid and refluxed for 9 hours. The reaction mixture was left stand for cooling to 35° C. and neutralized with 8.8 g of n-butylamine, and then the methanol was evaporated to obtain an oily substance. The resulting oily substance was added with 643 g of toluene and 271 g of n-butylamine and the mixture was stirred with heating at 90° C. for 10 hours. The reaction mixture was added with 506 g of warm water and 130 g of 95% sulfuric acid to separate an oil, and the aqueous layer was removed. The oil layer was added with 1200 g of warm water, and the solvent was removed under ordinary pressure to obtain slurry of white solid. This solid was collected by filtration and dried in vacuo at 50° C. to obtain 2-ethylhexanoylglutamic acid dibutylamide.

(a) $^{13}$C-NMR peaks (solvent: $CDCl_3$): 12.04, 12.07, 13.74, 13.96, 13.99, 20.08, 20.11, 22.70, 22.74, 26.01, 29.83, 31.56, 31.60, 32.37, 33.05, 39.29, 39.53, 49.37, 52.53, 52.56, 171.29, 173.03, 176.66 (ppm)
(b) $^1$H-NMR peaks ($CDCl_3$) δ : 3.248 (m, 4H), 4.373 (m, 1H), 6.199 (brs, 1H), 7.079 (brs, 1H), 7.169 (brs, 1H)
(c) Wave number of infrared absorption spectrum: 3291.7, 2961.0, 2932.5, 1638.2, 1551.2, 1452.6 ($cm^{-1}$)
(d) MS: 382.3 $(M-H)^-$ Example 2

Preparation of N-octanoyl-L-glutamic acid dibutylamide 110 g of sodium glutamate monohydrate was dissolved in 140 g of water and 78 g of 27% aqueous sodium hydroxide and cooled to 10° C. The solution was added with 110 g of acetone and added dropwise with 87 g of octanoyl chloride and 90 g of 27% aqueous sodium hydroxide. The reaction mixture for the acylation was diluted with 100 g of water and neutralized with 64 g of 95% sulfuric acid to separate an oil. The aqueous layer was removed, and the oil layer was concentrated under reduced pressure to obtain an oily substance. The resulting oily substance was dissolved in 742 g of methanol, and the solution was added with 6.2 g of 95% sulfuric acid and refluxed for 9 hours. The reaction mixture was left stand for cooling to 35° C. and neutralized with 10.5 g of n-butylamine, and then the methanol was evaporated to obtain an oily substance. The resulting oily substance was added with 630 g of toluene and 191 g of n-butylamine and the mixture was stirred with heating at 90° C. for 10 hours. The reaction mixture was added with 500 g of warm water and 178 g of 95% sulfuric acid to separate an oil, and the aqueous layer was removed. The oil layer was added with 645 g of warm water, and the solvent was removed under ordinary pressure to obtain slurry of white solid. The resulting solid was collected by filtration and dried in vacuo at 50° C. to obtain octanoylglutamic acid dibutylamide.
(a) $^{13}$C-NMR peaks: 14.10, 14.43, 20.44, 22.98, 26.07, 29.38, 29.61, 29.86, 31.92, 31.97, 32.06, 33.44, 37.07, 39.69, 39.88, 52.91, 171.61, 173.33, 174.17 (ppm)
(b) $^1$H-NMR peaks (CDCl$_3$) δ : 3.247 (m, 4H), 4.360 (m, 1H), 6.201 (brs, 1H), 6.987 (brs, 1H), 7.039 (brs, 1H)
(c) Wave number of infrared absorption spectrum: 3292.8, 2958.3, 2930.4, 1640.1, 1543.0, 1450.3 (cm$^{-1}$)
(d) MS: 382.3 (M–H)$^-$ Example 3

Preparation method of N-decanoyl-L-glutamic acid dibutylamide

In a manner similar to that of the aforementioned Example 1, N-decanoyl-L-glutamic acid dibutylamide was prepared.
(a) $^{13}$C-NMR peaks: 14.10, 14.47, 20.44, 20.48, 23.04, 26.07, 29.65, 29.67, 29.73, 29.83, 29.88, 31.92, 31.97, 32.24, 37.08, 39.70, 39.88, 52.90, 171.60, 173.33, 174.17 (ppm)
(b) $^1$H-NMR peaks (CDCl$_3$) δ : 3.250 (m, 4H), 4.360 (m, 1H), 6.190 (brs, 1H), 6.980 (brs, 1H), 7.030 (brs, 1H)
(c) Wave number of infrared absorption spectrum: 3294.8, 2959.0, 2927.5, 1637.9, 1556.0, 1466.6 (cm$^{-1}$)
(d) MS: 410.5 (M–H)$^-$ Ethyloylglutamic acid dibutylamide, hexanoylglutamic acid dibutylamide, myristoylglutamic acid dibutylamide and palmitoylglutamic acid dibutylamide used in the following comparative examples were produced in a similar manner.

Examples 4 to 6

Preparation of Gel Compositions 0.2 g of each N-acylglutamic acid dibutylamide shown in Table 1 was added to 20 g of each oil and dissolved by heating on an oil bath at 150° C., and then the resulting solution was left stand at 23° C. for 15 hours for cooling to obtain each gel composition. Gel strength of each of the resulting gel compositions was measured by using a rheometer (FUDOH RHEO METER NRM-2010-J-CW). An adapter for plume and viscoelasticity, 10 φ, was used, and the sample stage velocity was 6 cm/min. The results are shown in Table 1. As clearly understandable from the results shown in Table 1, N-2-(R,S)-ethylhexanoyl-L-glutamic acid dibutylamide, N-octanoyl-L-glutamic acid dibutylamide and N-decanoyl-L-glutamic acid dibutylamide have higher gel forming ability than the other gelling agents and can exert superior gel forming ability irrespective of a type of an oil.

TABLE 1

Gelling ability of various N-acylglutamic acid dibutylamides

| Gel composition | Acyl group | IPM | TOG | Liquid paraffin |
|---|---|---|---|---|
| Example 4 | Octanoyl | 99 | 156 | 136 |
| Example 5 | 2-Ethylhexanoyl | 175 | 209 | 145 |
| Example 6 | Decanoyl | 120 | 183 | 154 |
| Comparative Example 1 | Acetyl | 18 | 48 | Insoluble |
| Comparative Example 2 | Hexanoyl | Not gelled | Not gelled | Insoluble |
| Comparative Example 3 | Dodecanoyl (lauroyl) | 95 | 116 | 92 |
| Comparative Example 4 | Tetradecanoyl (myristoyl) | 67 | 72 | 80 |
| Comparative Example 5 | Pentadecanoyl | — | — | 30 |

IPM: Isopropyl myristate
TOG: Triocanoic acid glyceride
Unit: gel strength (g/cm$^2$)

Examples 7 to 10

Preparation of Gel Compositions 0.4 g of each gelling agent shown in Table 2 was added to 20 g of an oil and dissolved by heating on an oil bath at 150° C., and then the resulting solution was left stand at 23° C. for 15 hours for cooling to obtain gel compositions. Gel strength of each of the resulting gel compositions was measured by using a rheometer (FUDOH RHEO METER NRM-2010-J-CW). An adapter for plume and viscoelasticity, 10 φ, was used, and the sample stage velocity was 6 cm/min. Further, transparency of each of the resulting gel compositions was determined by visual inspection. The results are shown in Table 2. It is understandable that the gel compositions of Examples 7 to 9 have higher gel strength than the gel compositions of Comparative Examples 6 to 8. Further, it is also understandable that the gel compositions of Examples 8 to 10 have higher transparency than the gel compositions of the comparative examples.

TABLE 2

Gelling ability of various N-acylglutamic acid dibutylamides

| | Example 7 | Example 8 | Example 9 | Example 10 | Comparative Example 6 | Comparative Example 7 | Comparative Example 8 |
|---|---|---|---|---|---|---|---|
| N-2-Ethylhexanoylglutamic acid dibutylamide (Compound of Example 1) | 0.4 | 0.3 | 0.2 | 0.1 | — | — | — |
| N-Lauroylglutamic acid dibutylamide | — | 0.1 | 0.2 | 0.3 | 0.4 | 0.15 | — |
| 12-Hydroxystearic acid | — | — | — | — | — | 0.25 | 0.4 |
| Octyldodecanol | 4 | 4 | 4 | 4 | 4 | 4 | 4 |
| Cyclometicon D-5* | 16 | 16 | 16 | 16 | 16 | 16 | 16 |

TABLE 2-continued

Gelling ability of various N-acylglutamic acid dibutylamides

|  | Example 7 | Example 8 | Example 9 | Example 10 | Comparative Example 6 | Comparative Example 7 | Comparative Example 8 |
|---|---|---|---|---|---|---|---|
| Gel strength (g/cm$^2$) | 650 | 380 | 400 | 190 | 330 | 280 | 0 |
| Transparency | Opaque | Translucent | Translucent | Translucent | Opaque | Opaque | Opaque |

*TORAY-DOW CORNING SILICONE CORP., SH245

Examples 11 and 12

Preparation of Antiperspirant Gel Sticks

Each gelling agent shown in Table 3 was dissolved in an oil by heating, then the resulting solution added with aluminum zirconium trichlorohydrex glycine and left for cooling with stirring to obtain an antiperspirant gel stick. Gel strength of each of the resulting antiperspirant gel sticks was measured by using a rheometer (FUDOH RHEO METER NRM-2010-J-CW). An adapter for plume and viscoelasticity, 10 φ, was used, and the sample stage velocity was 6 cm/min. The results are shown in Table 3. The results indicate that the gel sticks of Examples 11 and 12 have higher gel strength than the gel sticks of the comparative example, and thus superior antiperspirants is obtainable.

TABLE 3

Gelling ability of various N-acylglutamic acid dibutylamides

|  | Comparative Example 9 | Example 11 | Example 12 |
|---|---|---|---|
| N-Lauroylglutamic acid dibutylamide | 2 | 1 | — |
| N-2-Ethylhexanoylglutamic acid dibutylamide (Compound of Example 1) | — | 1 | 2 |
| 12-Hydroxystearic acid | 7 | 7 | 7 |
| Octyldodecanol | 14 | 14 | 14 |
| Cyclometicon D-5* | 48 | 48 | 48 |
| Aluminum zirconium trichlorohydrex glycine | 26 | 26 | 26 |
| Gel strength (g/cm$^2$) | 1847 | 2250 | 2650 |

*TORAY-DOW CORNING SILICONE CORP., SH245
**Westwood Chemical Corporation, Westchlor ZR 30B DM CP-5

Example 13

Preparation of Lipstick

A lipstick was prepared in a conventional manner by using the composition shown in Table 4.

TABLE 4

Lipstick

|  | Example 13 |
|---|---|
| Octyl palmitate | 14 |
| Lanolin | 8.5 |
| Isopropyl palmitate | 8.5 |
| Cetyl ricinoleate | 5 |
| Dimeric acid isopropyl ester | 13 |
| N-2-Ethylhexanoylglutamic acid dibutylamide | 1.5 |
| Red No. 223 | 12 |

TABLE 4-continued

Lipstick

|  | Example 13 |
|---|---|
| Lecithin | 0.7 |
| Polyethylene glycol distearate | 3.25 |
| Sorbitan monooleate | 5 |
| Choresteryl hydroxystearate | 2 |
| Dipentaerythritol | 2 |
| Glycerol | 9 |
| Panthenol | 1 |
| Ozokerite | 3.5 |
| Paraffin | 3.25 |
| Candelilla wax | 4.65 |
| Bees wax | 3 |
| Tocophenol | 0.1 |
| Propylparaben | 0.05 |
|  | (Weight %) |

The lipstick obtained was superior in strength and excellently free from sweating.

Example 14

Preparation of Transparent Lipstick

A transparent lipstick was prepared in a conventional manner by using the composition shown in Table 5.

TABLE 5

Stick type transparent lipstick

|  | Example 14 |
|---|---|
| N-2-Ethylhexanoylglutamic acid dibutylamide | 3 |
| Aliphatic acid starch ester | 5 |
| 12-Hydroxystearic acid | 1.5 |
| Diglyceryl triisostearate | 80.45 |
| Rosin acid pentaerythritol ester | 10 |
| Red No. 223 | 0.05 |
|  | (Weight %) |

The transparent lipstick obtained was superior in strength, and moreover, had highly transparent appearance and satisfactory stability.

Example 15

Preparation of Candle

A candle was prepared in a conventional manner by using the composition shown in Table 6.

TABLE 6

| | Candle |
| --- | --- |
| | Example 15 |
| Hydrogenated polyisobutene* | 87.4 |
| Hydrogenated polyisobutene** | 6.7 |
| Isostearyl alcohol | 5.5 |
| N-2-Ethylhexanoylglutamic acid dibutylamide | 0.4 |
| | (Weight %) |

*Panalane ™ H300E (Amoco Chemical)
**Panalane ™ L14E (Amoco Chemical)

The candle obtained was superior in strength and had highly transparent appearance.

What is claimed is:

1. A gel composition comprising
   (a) N-lauroyl-L-glutamic acid dibutylamide,
   (b) N-2-ethylhexanoyl-L-glutamic acid dibutylamide, and
   (c) at least one oil,
   wherein the ratio of the total weight of N-lauroyl-L-glutamic acid dibutylamide and the weight of N-2-ethylhexanoyl-L-glutamic acid dibutylamide is 3:1 to 1:3.

2. The gel composition according to claim 1, wherein the ratio of the total weight of N-lauroyl-L-glutamic acid dibutylamide and the weight of N-2-ethylhexanoyl-L-glutamic acid dibutylamide is 1:1.

3. The gel composition according to claim 1, which is a translucent composition.

4. The gel composition according to claim 1, which further comprises
   (d) at least one antiperspirant active ingredient.

5. A cosmetic comprising a gel composition according to claim 1.

6. The gel composition according to claim 1, wherein said N-lauroyl-L-glutamic acid dibutylamide is in a hydrate form.

7. The gel composition according to claim 1, wherein said N-lauroyl-L-glutamic acid dibutylamide is in a crystal form.

8. The cosmetic according to claim 5, further comprising one or more additives selected from the group consisting of a chelating agent, a gelling agent, a surfactant, an amino acid, a polyhydric alcohol, a polyamino acid, a water-soluble polymer, a sugar alcohol, a lower alcohol, an animal extract, a plant extract, a nucleic acid, a vitamin, an enzyme, an anti-inflammatory agent, an antibacterial agent, a preservative, an antioxidant, an ultraviolet absorber, an antiperspirant, a pigment, a dye, an oxidation dye, an organic fine particle, an inorganic fine particle, a pH adjusting agent, a pearling agent, and a wetting agent.

9. A cosmetic comprising a gel composition according to claim 4.

10. The cosmetic according to claim 9, further comprising one or more additives selected from the group consisting of a chelating agent, a gelling agent, a surfactant, an amino acid, a polyhydric alcohol, a polyamino acid, a water-soluble polymer, a sugar alcohol, a lower alcohol, an animal extract, a plant extract, a nucleic acid, a vitamin, an enzyme, an anti-inflammatory agent, an antibacterial agent, a preservative, an antioxidant, an ultraviolet absorber, a pigment, a dye, an oxidation dye, an organic fine particle, an inorganic fine particle, a pH adjusting agent, a pearling agent, and a wetting agent.

11. The gel composition according to claim 6, wherein said N-2-ethylhexanoyl-L-glutamic acid dibutylamide is in a hydrate form.

12. The gel composition according to claim 7, wherein said N-2-ethylhexanoyl-L-glutamic acid dibutylamide is in a crystal form.

13. The gel composition according to claim 1, wherein said N-2-ethylhexanoyl-L-glutamic acid dibutylamide is in a hydrate form.

14. The gel composition according to claim 1, wherein said N-2-ethylhexanoyl-L-glutamic acid dibutylamide is in a crystal form.

* * * * *